(12) United States Patent  (10) Patent No.: US 11,598,744 B2
Yamazaki                  (45) Date of Patent:      Mar. 7, 2023

(54) SENSOR

(71) Applicant: KABUSHIKI KAISHA TOSHIBA, Tokyo (JP)

(72) Inventor: Hiroaki Yamazaki, Yokohama Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 106 days.

(21) Appl. No.: 17/187,702

(22) Filed: Feb. 26, 2021

(65) Prior Publication Data
US 2022/0082522 A1  Mar. 17, 2022

(30) Foreign Application Priority Data
Sep. 16, 2020 (JP) ............................. JP2020-155480

(51) Int. Cl.
*G01N 33/00*  (2006.01)
*G01N 27/22*  (2006.01)

(52) U.S. Cl.
CPC ......... *G01N 27/227* (2013.01); *G01N 33/005* (2013.01); *G01N 2027/222* (2013.01)

(58) Field of Classification Search
CPC .... G01N 27/227; G01N 33/005; G01N 33/00; G01N 27/22; G01N 2027/222; G01N 2027/22; G01N 27/286; G01N 27/3275; G01N 27/02; G01N 33/0036; G01N 33/0031; G01N 33/0004; G01N 33/0009; G01N 1/22
See application file for complete search history.

(56) References Cited

U.S. PATENT DOCUMENTS

2019/0086377 A1* 3/2019 Ikehashi ............. G01N 27/221
2021/0109071 A1* 4/2021 Hayashi ............. G01N 33/0073

FOREIGN PATENT DOCUMENTS

EP  3 534 154 A1    9/2019
JP  2019-56607 A    4/2019
JP  2019-152451 A   9/2019

* cited by examiner

*Primary Examiner* — Tarun Sinha
*Assistant Examiner* — James I Burris
(74) *Attorney, Agent, or Firm* — Finnegan, Henderson, Farabow, Garrett & Dunner, LLP

(57) ABSTRACT

According to one embodiment, a sensor includes a sensor part and a first circuit. The sensor part includes a base body, a fixed electrode fixed to the base body, a supporter fixed to the base body, and a movable part supported by the supporter. The movable part includes a movable region including a movable electrode facing the fixed electrode, and a first support region provided between the movable region and the supporter. The first support region includes a first electrode, and a second electrode insulated from the first electrode. The first circuit is configured to perform a first operation of applying a voltage between the first electrode and the second electrode.

20 Claims, 8 Drawing Sheets

SENSOR

CROSS-REFERENCE TO RELATED APPLICATIONS

This application is based upon and claims the benefit of priority from Japanese Patent Application No. 2020-155480, filed on Sep. 16, 2020; the entire contents of which are incorporated herein by reference.

FIELD

Embodiments of the invention generally relate to a sensor.

BACKGROUND

For example it is desirable to improve the detection performance of a sensor.

DETAILED DESCRIPTION

Figure 1A:
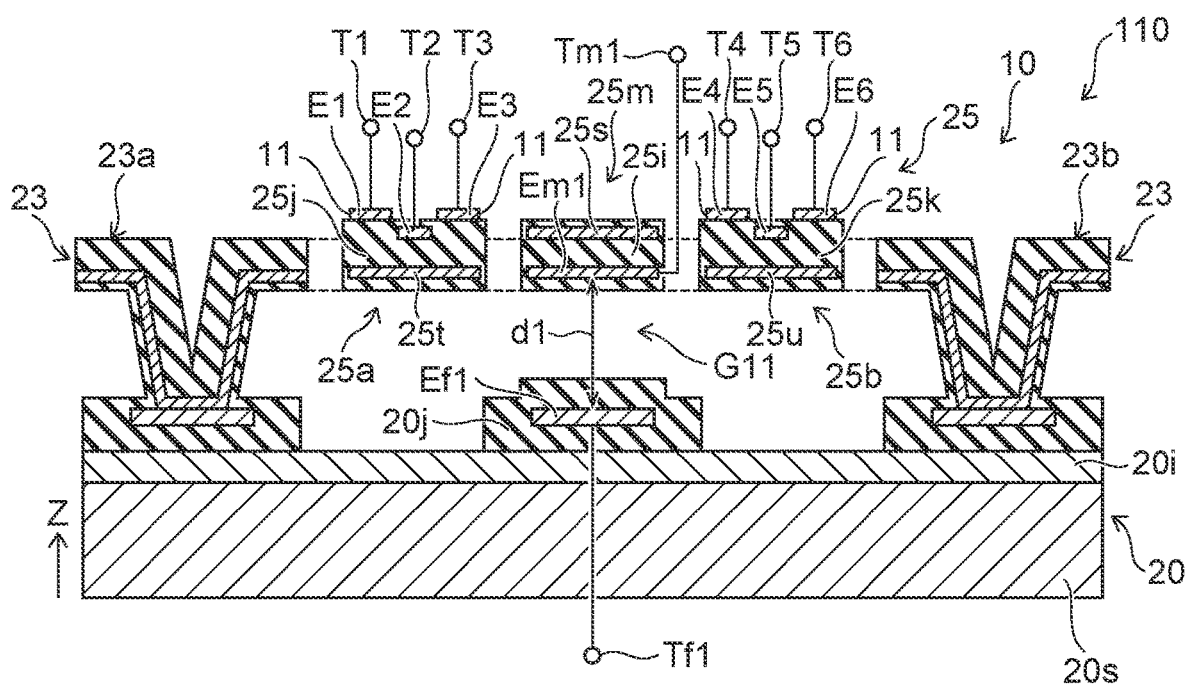
FIGS. 1A and 1B are schematic views illustrating a sensor according to a first embodiment.

According to one embodiment, a sensor includes a sensor part and a first circuit. The sensor part includes a base body, a fixed electrode fixed to the base body, a supporter fixed to the base body, and a movable part supported by the supporter. The movable part includes a movable region including a movable electrode facing the fixed electrode, and a first support region provided between the movable region and the supporter. The first support region includes a first electrode, and a second electrode insulated from the first electrode. The first circuit is configured to perform a first operation of applying a voltage between the first electrode and the second electrode.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously or illustrated in an antecedent drawing are marked with like reference numerals, and a detailed description is omitted as appropriate.

First Embodiment

Figure 1B:
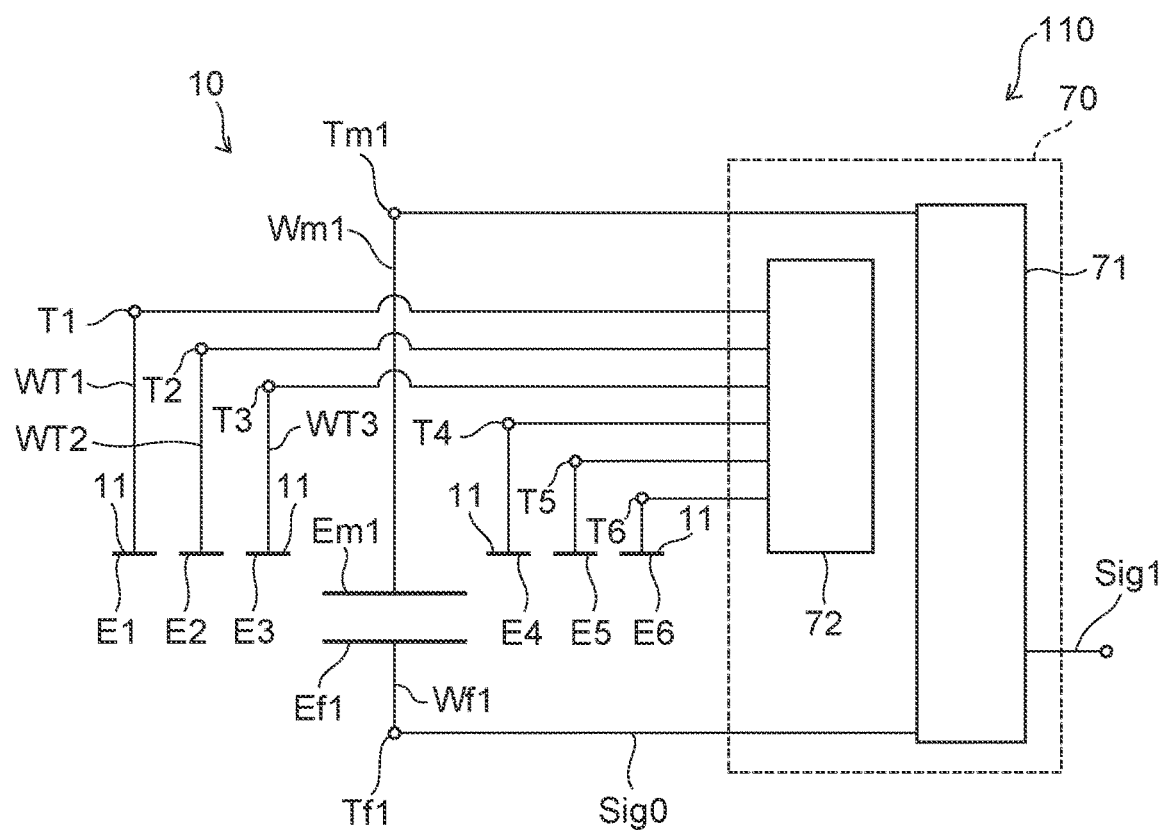

FIGS. 1A and 1B are schematic views illustrating a sensor according to a first embodiment, FIG. 1A is a schematic cross-sectional view of the sensor 110 according to the embodiment. FIG. 1B is a schematic circuit diagram of the sensor 110. The sensor 110 includes a sensor part 10 and a first circuit 70 (referring to FIG. 1B), The first circuit 70 is not illustrated in FIG. 1A. For example, the sensor 110 is a gas sensor that is configured to detect a gas including a first element (e.g., hydrogen).

As shown in FIG. 1A, the sensor part 10 includes a base body 20, a fixed electrode Ef1, a supporter 23, and a movable part 25. The fixed electrode Ef1 is fixed to the base body 20. The supporter 23 is fixed to the base body 20. The movable part 25 is supported by the supporter 23, The movable part 25 is separated from the base body 20. A gap G11 is provided between the movable part 25 and the base body 20. The movable part 25 is, for example, a film portion.

The movable part 25 includes a first support region 25a and a movable region 25m. The first support region 25a is located between the movable region 25m and the supporter 23 (a first portion 23a).

The movable region 25m includes a movable electrode Em1. The movable electrode Em1 faces the fixed electrode Ef1. The movable electrode Em1 is electrically connected to a movable electrode terminal Tm1, For example, the connection is performed by wiring Wm1 (referring to FIG. 1B). The fixed electrode Ef1 is electrically connected to a fixed electrode terminal Tf1. For example, the connection is performed by wiring Wf1 (referring to FIG. 1B). At least a portion of the wiring may include, for example, a conductive member included in the supporter 23.

The direction from the fixed electrode Ef1 toward the movable electrode Em1 is taken as a Z-axis direction (a first direction). One direction perpendicular to the Z-axis direction is taken as an X-axis direction, A direction perpendicular to the Z-axis direction and the X-axis direction is taken as a Y-axis direction. The first support region 25a includes a first electrode E1 and a second electrode E2. The second electrode E2 is electrically insulated from the first electrode E1. For example, the first support region 25a includes an insulating portion 25j. The insulating portion 25j includes, for example, SiN. The insulating portion 25j is located between the first electrode E1 and the second electrode E2. The first electrode E1 is electrically connected to a first terminal T1. For example, the connection is performed by wiring WT1 (referring to FIG. 1B). The second electrode E2 is electrically connected to a second terminal T2. For example, the connection is performed by wiring WT2 (referring to FIG. 1B), At least a portion of the wiring may include, for example, a conductive member included in the supporter 23.

The sensor 110 includes, for example, a first film 11. In the example, the first electrode E1 also is included in the first film 11, According to the embodiment, the first film 11 may be separate from the first electrode E1. For example, the first film 11 is located at the front surface of the movable part 25. For example, the first film 11 is exposed. The first film 11 can efficiently contact the gas including the first element. For example, the first film 11 (the first electrode E1) can store the first element (e.g., hydrogen, etc.). For example, the first element (e.g., hydrogen, etc.) is adsorbed to the first film 11. The characteristics of the first film 11 change when the first film 11 stores the first element. For example, when the first film 11 stores the first element, the first film 11 expands, and the volume of the first film 11 increases. A characteristic (e.g., the volume, etc.) of the first film can change according to the change of the concentration of the first element included in the gas at the periphery of the first film 11. For example, the shape of the first film 11 (e.g., the first electrode E1) changes according to the concentration of the first element included in the gas around the sensor part 10. The existence or absence of the first element or the concentration of the first element at the periphery of the first film 11 can be detected by detecting a signal corresponding to the change of the characteristics of the first film 11.

The movable region 25m is separated from the fixed electrode Ef1. The gap G11 is located between the fixed electrode Ef1 and the movable electrode Em1. The movable region 25m that includes the movable electrode Em1 is supported in a support region including the first film 11 (the first electrode E1). For example, the first film 11 (the first electrode E1) is fixed with respect to the movable electrode Em1. An electrical signal that is generated between the fixed electrode Ef1 and the movable electrode Em1 changes according to the change of the characteristics (e.g., the volume) of the first film 11. The existence or absence of the first element or the concentration of the first element at the periphery of the first film 11 can be detected by detecting the change of the electrical signal.

For example, the movable part 25 (e.g., a diaphragm) that Includes the first film 11 deforms when the first film 11 expands. The deformation of the movable part 25 is caused by stress generated by the expansion of the first film 11. A distance d1 between the fixed electrode Ef1 and the movable electrode Em1 changes when the movable part 25 deforms. The electrostatic capacitance between the fixed electrode Ef1 and the movable electrode Em1 changes when the distance d1 between the fixed electrode Ef1 and the movable electrode Em1 changes. By detecting the change of the electrostatic capacitance, the existence or absence of the first element or the concentration of the first element at the periphery of the first film 11 can be detected. In the example, the sensor part 10 has a MEMS (Micro Electro Mechanical Systems) structure.

Thus, in one example, the distance d1 (the distance of the gap G11) changes according to the concentration of the first element included in the gas around the sensor part 10. The first dement can be detected by detecting the change of the distance d1 as the change of the electrostatic capacitance. According to the embodiment, other characteristics (e.g., the conductivity, etc.) of the first film 11 may change according to the concentration of the first element included in the gas at the periphery of the sensor part 10. The first dement can be detected by detecting the change of the other characteristic.

As shown in FIG. 1B, the first circuit 70 includes, for example, a detection circuit 71. The detection circuit 71 is electrically connected to the fixed electrode terminal Tf1 and the movable electrode terminal Tm1. The detection circuit 71 is electrically connected to the movable electrode Em1 via the movable electrode terminal Tm1, The detection circuit 71 is electrically connected to the fixed electrode Ef1 via the fixed electrode terminal Tf1. The detection circuit 71 is configured to output a detection signal Sig1. The detection signal Sig1 changes according to the concentration of the first dement included in the gas around the sensor part 10.

For example, a sensor signal Sig0 can be output from the sensor part 10. The sensor signal Sig0 is generated between the fixed electrode Ef1 and the movable electrode Em1. For example, the sensor signal Sig0 is generated between the fixed electrode terminal Tf1 and the movable electrode terminal Tm1. The sensor signal Sig0 changes according to the concentration of the first element included in the gas around the sensor part 10. For example, the detection signal Sig1 that is output from the detection circuit 71 corresponds to the sensor signal Sig0. The detection circuit 71 can process the sensor signal Sig0 and output the processed sensor signal Sig0 as the detection signal Sig1. The processing may include, for example, amplification. The amplification may include deriving a difference between a reference value.

The first circuit 70 includes, for example, a voltage circuit 72, The voltage circuit 72 is electrically connected to the first electrode E1 via the first terminal T1. The voltage circuit 72 is electrically connected to the second electrode E2 via the second terminal T2. The first circuit 70 (the voltage circuit 72) is configured to perform a first operation of applying a voltage between the first electrode E1 and the second electrode E2.

For example, a first substance (including, for example, at least one of water molecules, sulfur, nitrogen, or siloxane (HMDS)) in the gas has polarity. An electric field can be generated between the first electrode E1 and the second electrode E2 by the first operation. Thereby, for example, an electric field can be generated around the first film 11 (in the example, the first electrode E1). For example, the first substance can be controlled by the generated electric field. The detection performance of the sensor can be improved thereby.

The first circuit 70 may include, for example, a CPU (Central Processing Unit), etc. At least a portion of the first circuit 70 may be included in the sensor 110. At least a portion of the first circuit 70 may be provided separately from the sensor 110.

In the example, the base body 20 includes a substrate 20s, an insulating film 20i, and an insulating portion 20j. The substrate 20s is, for example, a Si substrate. The insulating film 20i is located on the substrate 20s; and the insulating portion 20j is located on the insulating film 20i. The insulating portion 20j includes, for example, SiN. For example, the insulating portion 20j is located at the upper and lower surfaces of the fixed electrode Ef1.

The supporter 23 is located on the insulating film 20i, The supporter 23 includes, for example, SiN. The gap G11 can be formed by the supporter 23 supporting the movable part 25. The distance d1 is changeable thereby. The movable region 25m of the movable part 25 includes an insulating portion 25i. The insulating portion 25i includes, for example, SiN. For example, the insulating portion 25i is located at the upper and lower surfaces of the movable electrode Enol.

In the example as shown in FIG. 1A, the first support region 25a further includes a third electrode E3. The third electrode E3 is electrically insulated from the second electrode E2. The third electrode E3 is electrically connected to a third terminal T3. For example, the connection is performed by wiring WT3. At least a portion of the wiring may include a conductive member included in the supporter 23. In the example, the third electrode E3 also is included in the first film 11. The existence or absence of the first element or the concentration of the first element at the periphery of the first film 11 can be detected according to the change of the characteristics of the first film 11 (the third electrode E3). For example, when the third electrode E3 is provided in addition to the first electrode E1, the detection sensitivity of the first element can be increased. According to the embodiment, the first film 11 may be separate from the third electrode E3.

As shown in FIG. 1B, the voltage circuit 72 is electrically connected to the third electrode E3 via the third terminal T3, For example, the first operation of the first circuit 70 includes applying a voltage between the second electrode E2 and the third electrode E3. Thereby, an electric field can be generated between the third electrode E3 and the second electrode E2. For example, the first substance around the first film 11 can be controlled by the generated electric field. For example, when the third electrode E3 is provided in addition to the first electrode E1, the first substance is more easily controlled. The detection performance of the sensor can be improved thereby.

In the example as shown in FIG. 1A, the movable part 25 further includes a second support region 25b. The movable region 25m is between the first support region 25a and the second support region 25b. The second support region 25b is between the movable region 25m and the supporter 23 (a second portion 23b).

The second support region 25b includes a fourth electrode E4, a fifth electrode E5, and a sixth electrode E6. The fifth electrode E5 is electrically insulated from the fourth and sixth electrodes E4 and E6. For example, the second support region 25b includes an insulating portion 25k. The insulating portion 25k includes, for example, SiN. The insulating portion 25k is located between the fourth electrode E4 and the fifth electrode E5 and between the fifth electrode E5 and the sixth electrode E.

The fourth electrode E4 is electrically connected to a fourth terminal T4. The fifth electrode E5 is electrically connected to a fifth terminal T5. The sixth electrode E6 is electrically connected to a sixth terminal T6. In the example, the fourth electrode E4 and the sixth electrode E6 also are included in the first film 11. The existence or absence of the first element or the concentration of the first element at the periphery of the first film 11 can be detected according to the change of the characteristics of the first film 11 (the fourth electrode E4 and the sixth electrode E6). For example, when the fourth electrode E4 and the sixth electrode E6 are provided, the detection sensitivity of the first element can be further increased. According to the embodiment, the first film 11 may be separate from the fourth and sixth electrodes E4 and E6. As shown in FIG. 1B, the voltage circuit 72 is electrically connected to the fourth electrode E4 via the fourth terminal T4. The voltage circuit 72 is electrically connected to the fifth electrode E5 via the fifth terminal T5. The voltage circuit 72 is electrically connected to the sixth electrode E6 via the sixth terminal T6. For example, the first operation of the first circuit 70 includes applying a voltage between the fourth electrode E4 and the fifth electrode E5, For example, the first operation of the first circuit 70 includes applying a voltage between the fifth electrode E5 and the sixth electrode E6. Thereby, an electric field can be generated between the fourth electrode E4 and the fifth electrode E5 and between the fifth electrode E5 and the sixth electrode E6. For example, the first substance around the first film 11 can be controlled by the generated electric field. The detection performance of the sensor can be improved thereby. The fourth to sixth electrodes E4 to E6 may have configurations similar to the first to third electrodes E1 to E3.

The first film 11 (in the example, the first electrode E1, the third electrode E3, the fourth electrode E4, the sixth electrode E6, etc.) includes, for example, a second element. The second element includes at least one selected from the group consisting of Pd, Pt, and Au. When the first element is hydrogen, the second element may function as a catalyst.

The first film 11 (in the example, the first electrode E1, the third electrode E3, the fourth electrode E4, the sixth electrode E6, etc.) may include, for example, a third element. The third element includes at least one selected from the group consisting of Si, P, and B. When the first element is hydrogen, for example, a high reaction rate is obtained by the first film 11 including the third element.

The first film 11 (in the example, the first electrode E1, the third electrode E3, the fourth electrode E4, the sixth electrode E6, etc.) may further include, for example, a fourth element. The fourth element includes at least one selected from the group consisting of Cu, Ag, Ni, Fe, and Cr. When the first element is hydrogen, for example, a high reaction rate is obtained by the first film 11 including the fourth element.

The movable electrode Em1, the fixed electrode Ef1, the second electrode E2, and the fifth electrode E5 includes, for example, at least one selected from the group consisting of Ti, Al, and TiN.

In the example, a conductive layer 25s is provided in the insulating portion 25i; a conductive layer 25t is provided in the insulating portion 25j; and a conductive layer 25u is provided in the insulating portion 25k. For example, the warp of the movable region 25m, the first support region 25a, and the second support region 25b can be adjusted thereby. For example, the conductive layer 25s, the conductive layer 25t, and the conductive layer 25u may have mesh configurations or may be omitted.

Figure 2A:
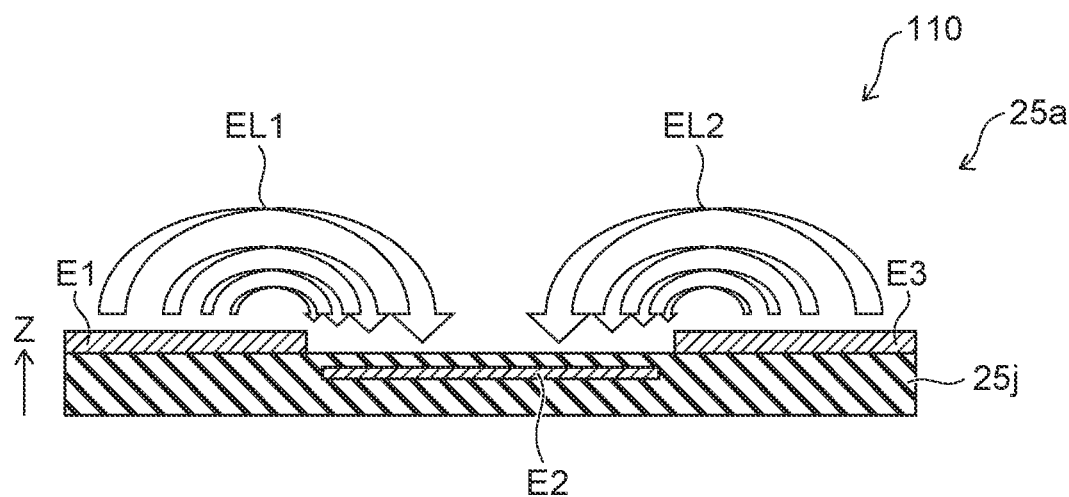
FIGS. 2A and 2B are schematic views illustrating a portion of the sensor according to the first embodiment.
Figure 2B:
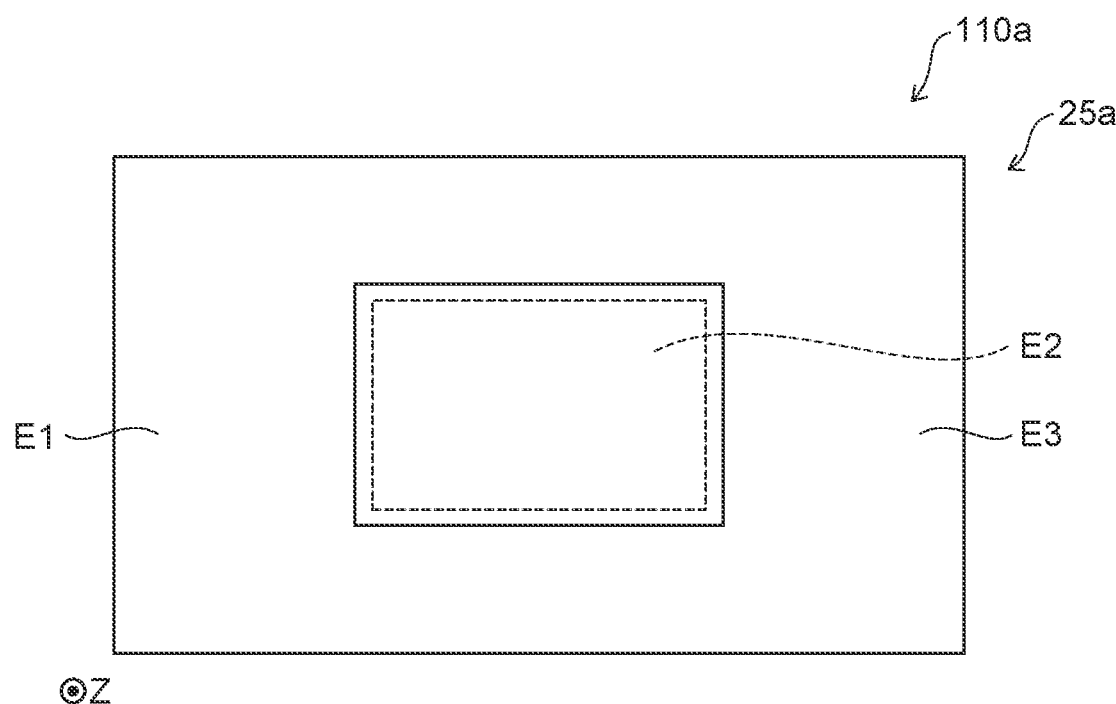

FIGS. 2A and 2B are schematic views illustrating a portion of the sensor according to the first embodiment.

FIG. 2A is a schematic cross-sectional view illustrating a portion of the sensor according to the first embodiment.

In the first operation, the potential of the first electrode E1 and the potential of the third electrode E3 are, for example, positive. In the first operation, the potential of the second electrode E2 is, for example, negative. In the first operation as shown in FIG. 2A, for example, an electric field EL1 from the first electrode E1 toward the second electrode E2 is generated. In the first operation, for example, an electric field EL2 from the third electrode E3 toward the second electrode E2 is generated. In the sensor, there are cases where the first substance is adhered or adsorbed to the first film 11 (in the example, the first electrode E1 and the third electrode E3) before the concentration of the first element is detected. It is considered that in such a case, the detection sensitivity may decrease or the response time may increase when detecting the concentration of the first element.

For example, when the first element is hydrogen, there are cases where the sensitivity of the sensor decreases if the humidity is high. It is considered that when the humidity is high, water molecules are adhered on the first film 11 before the concentration is detected. It is considered that in such a case, it is difficult for hydrogen to adsorb to the first film 11 when detecting the hydrogen concentration.

Conversely, according to the embodiment, the first substance can be controlled by the electric fields EL1 and EL2. For example, the adhesion of the first substance to the first film 11 can be suppressed by the electric fields EL1 and EL2 before detecting the concentration of the first element, etc. For example, the reduction of the detection sensitivity can be suppressed thereby. For example, at least a portion of the second electrode E2 does not overlap the first electrode E1 in the first direction (the Z-axis direction). Thereby, for example, the electric field is more easily generated at the front surface of the first support region 25a. For example, the direction of the electric field EL1 at the periphery of the first electrode E1 includes a component outward of the first support region 25a from the first electrode E1, For example, the adhesion or the adsorption of the first substance to the first electrode E1 can be suppressed thereby. For example, the first substance can easily be kept away from the first film 11 by the electric field. In the example, the second electrode E2 does not overlap the first electrode E1 in the first direction.

FIG. 23 is a schematic plan view illustrating a portion of another sensor according to the first embodiment. FIG. 23 shows the first electrode E1, the second electrode E2, and the third electrode E3 of the sensor 110a according to the first embodiment. In the example, the first electrode E1 and the third electrode E3 are continuous. The third electrode E3 may be a continuous body with the first electrode E1. For example, the first electrode E1 (and the third electrode E3) surround the second electrode E2 when viewed from the Z-axis direction. For example, the first electrode E1 (and the third electrode E3) are ring-shaped when viewed from the Z-axis direction. Similarly, the fourth electrode E4 and the sixth electrode E6 may be continuous. The fourth electrode E4 and the sixth electrode E6 may be a continuous body. The fourth electrode E4 (and the sixth electrode E6) may surround the fifth electrode E5 when viewed from the Z-axis direction. For example, the fourth electrode E4 (and the sixth electrode E6) are ring-shaped when viewed from the Z-axis direction. Otherwise, a description similar to that of the sensor 110 is applicable to the sensor 110a. The first electrode E1, the third electrode E3, the fourth electrode E4, and the sixth electrode E6 may be short-circuited and may have the same potential.

Figure 3A:
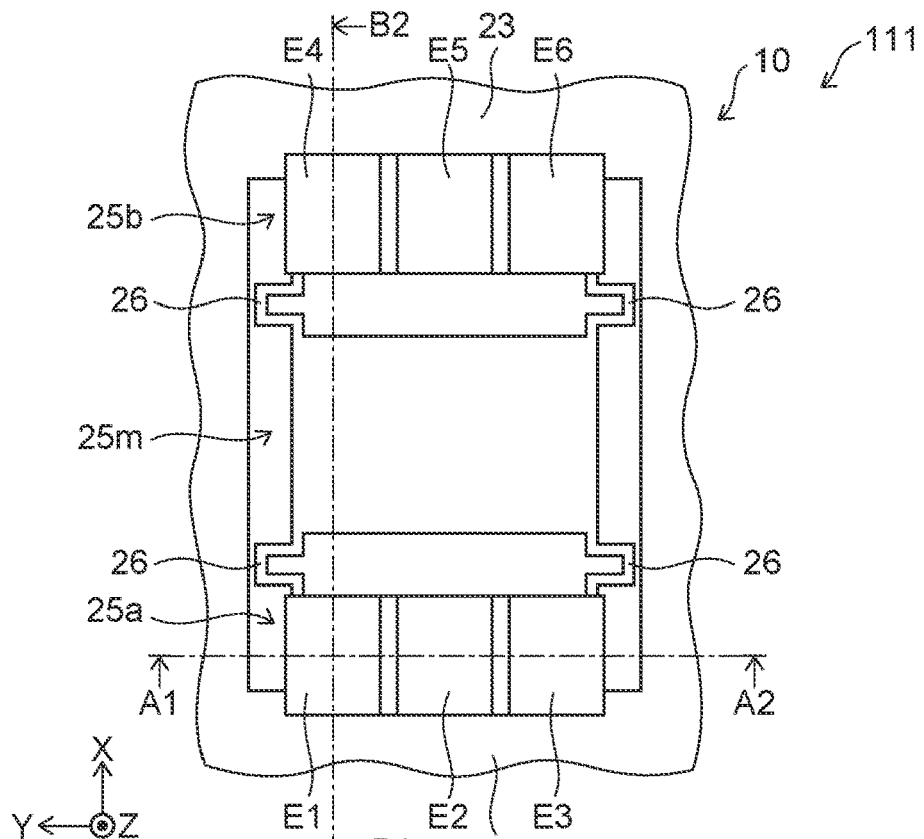
FIGS. 3A to 3C are schematic views illustrating a sensor according to the first embodiment.
Figure 3B:
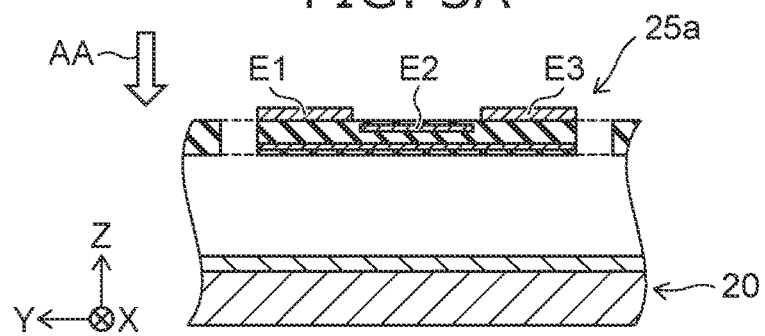
Figure 3C:
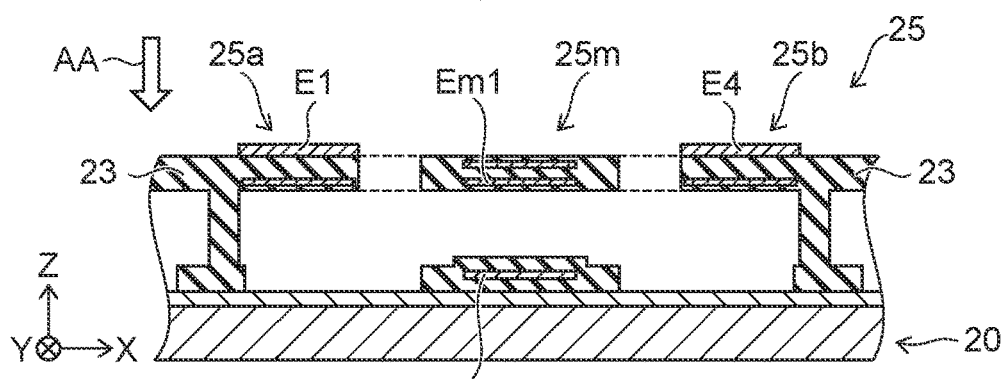

FIGS. 3A to 3C are schematic views illustrating a sensor according to the first embodiment.

FIG. 3A is a schematic plan view as viewed along arrow AA of FIGS. 3B and 3C. FIG. 3B is a line A1-A2 cross-sectional view of FIG. 3A. FIG. 3C is a line B1-B2 cross-sectional view of FIG. 3A. The sensor 111 according to the embodiment includes the sensor part 10 and the first circuit 70 (referring to FIG. 1B). The sensor part 10 includes the base body 20, the fixed electrode Ef1, the supporter 23, and the movable part 25, The movable part 25 includes the first support region 25a, the second support region 25b, and the movable region 25m. The movable region 25m includes the movable electrode Em1. The first support region 25a includes the first electrode E1, the second electrode E2, and the third electrode E. The second support region 25b includes the fourth electrode E4, the fifth electrode E5, and the sixth electrode E6. The movable part 25 may have multiple holes. For example, a gap between the movable part 25 and the base body 20 may be provided by etching a layer between the movable part 25 and the base body 20 through the multiple holes.

In the example as shown in FIG. 3A, a second direction (e.g., the X-axis direction) from the first support region 25a toward the movable region 25m crosses the first direction (the Z-axis direction). A third direction (e.g., the Y-axis direction) from the first electrode E1 toward the third electrode E3 crosses a plane including the first and second directions. When viewed in plan, for example, at least a portion of the second electrode E2 is between the first electrode E1 and the third electrode E3. As shown in FIGS. 3A and 313, the position in the third direction of at least a portion of the second electrode E2 is between the position in the third direction of the first electrode E1 and the position in the third direction of the third electrode E3. Thereby, for example, an appropriate electric field is easily generated in the first operation. For example, the second electrode E2 is not provided between the first electrode E1 and the movable region 25m. For example, the second electrode E2 is not provided between the third electrode E3 and the movable region 25m. Thereby, for example, the stress that is generated by the deformation of the first and third electrodes E1 and E3 is easily transferred to the movable part 25.

As shown in FIG. 3A, a fourth direction (e.g., the Y-axis direction) from the fourth electrode E4 toward the sixth electrode E6 crosses a plane including the first and second directions. The fourth direction may be parallel to the third direction. When viewed in plan, for example, at least a portion of the fifth electrode E5 is between the fourth electrode E4 and the sixth electrode E. The position in the fourth direction of at least a portion of the fifth electrode E5 is between the position in the fourth direction of the fourth electrode E4 and the position in the fourth direction of the sixth electrode E. For example, the fifth electrode E5 is not provided between the fourth electrode E4 and the movable region 25m. For example, the fifth electrode E5 is not provided between the sixth electrode E6 and the movable region 25m.

In the example as shown in FIG. 3A, the movable part 25 includes multiple connection portions 26. The multiple connection portions 26 are, for example, spring portions. The multiple connection portions 26 connect the first support region 25a and the movable region 25m. The multiple connection portions 26 connect the second support region 25b and the movable region 25m. The first support region 25a and the second support region 25b support the movable region 25m via the multiple connection portions 26. The widths of the multiple connection portions 26 are less than the width of the first electrode E1. The multiple connection portions 26 have bent shapes when viewed in plan. The multiple connection portions 26 include, for example, at least one of SiN or TiN.

Figure 4:
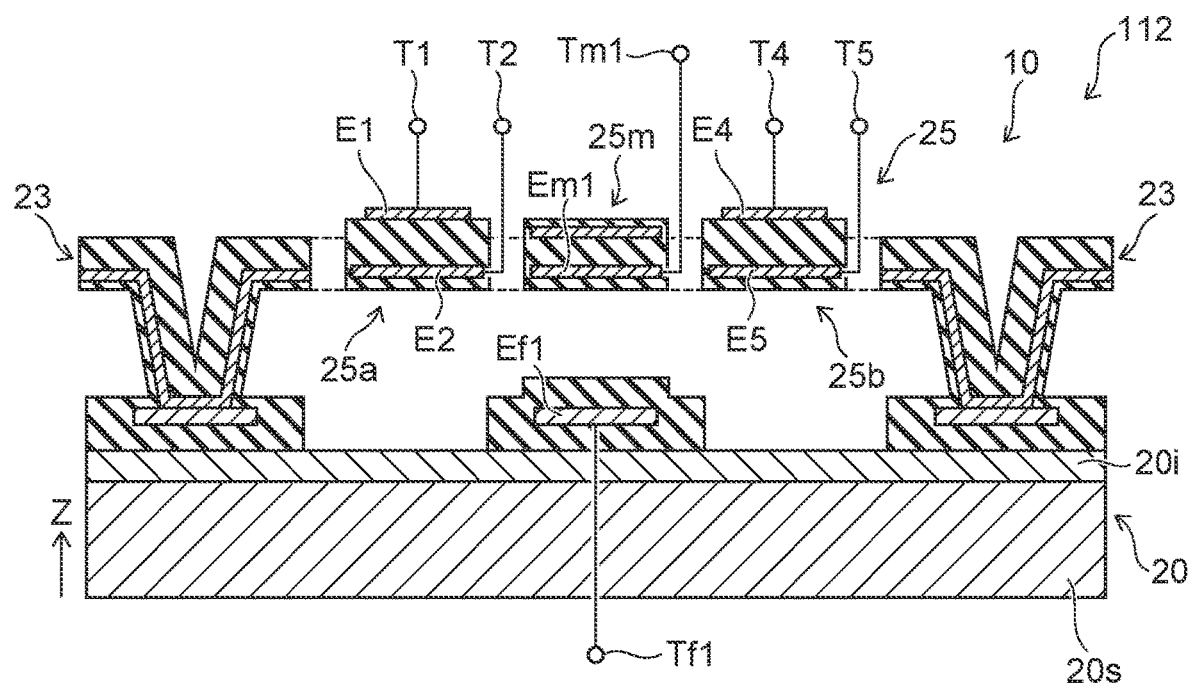
FIG. 4 is a schematic cross-sectional view illustrating a sensor according to the first embodiment.

FIG. 4 is a schematic cross-sectional view illustrating a sensor according to the first embodiment.

As shown in FIG. 4, the sensor part 10 and the first circuit 70 (referring to FIG. 1B) are provided in the sensor 112 as well. The sensor part 10 includes the base body 20, the fixed electrode Ef1, the supporter 23, and the movable part 25. The movable part 25 includes the first support region 25a, the second support region 25b, and the movable region 25m. The movable region 25m includes the movable electrode Enol. The first support region 25a includes the first electrode E1 and the second electrode E2. The second support region 25b includes the fourth electrode E4 and the fifth electrode E5.

In the example, the first electrode E1 overlaps the second electrode E2 in the first direction (the Z-axis direction). The entire first electrode E1 may overlap the second electrode E2 in the first direction. The fourth electrode E4 overlaps the fifth electrode E5 in the first direction. The entire fourth electrode E4 may overlap the fifth electrode E5 in the first direction. In the example as well, at least a portion of the second electrode E2 does not overlap the first electrode E1 in the first direction (the Z-axis direction). Thereby, for example, the electric field is more easily generated at the front surface of the movable part 25.

Second Embodiment

Figure 5A:
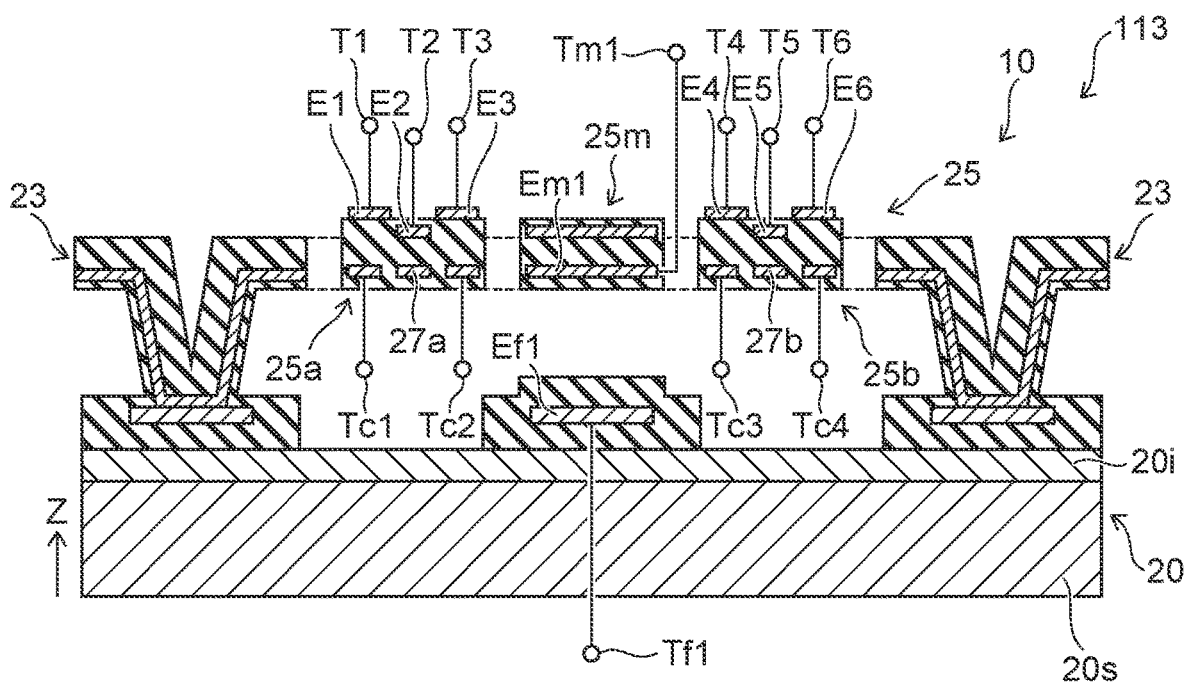
FIGS. 5A and 5B are schematic views illustrating a sensor according to a second embodiment.
Figure 5B:
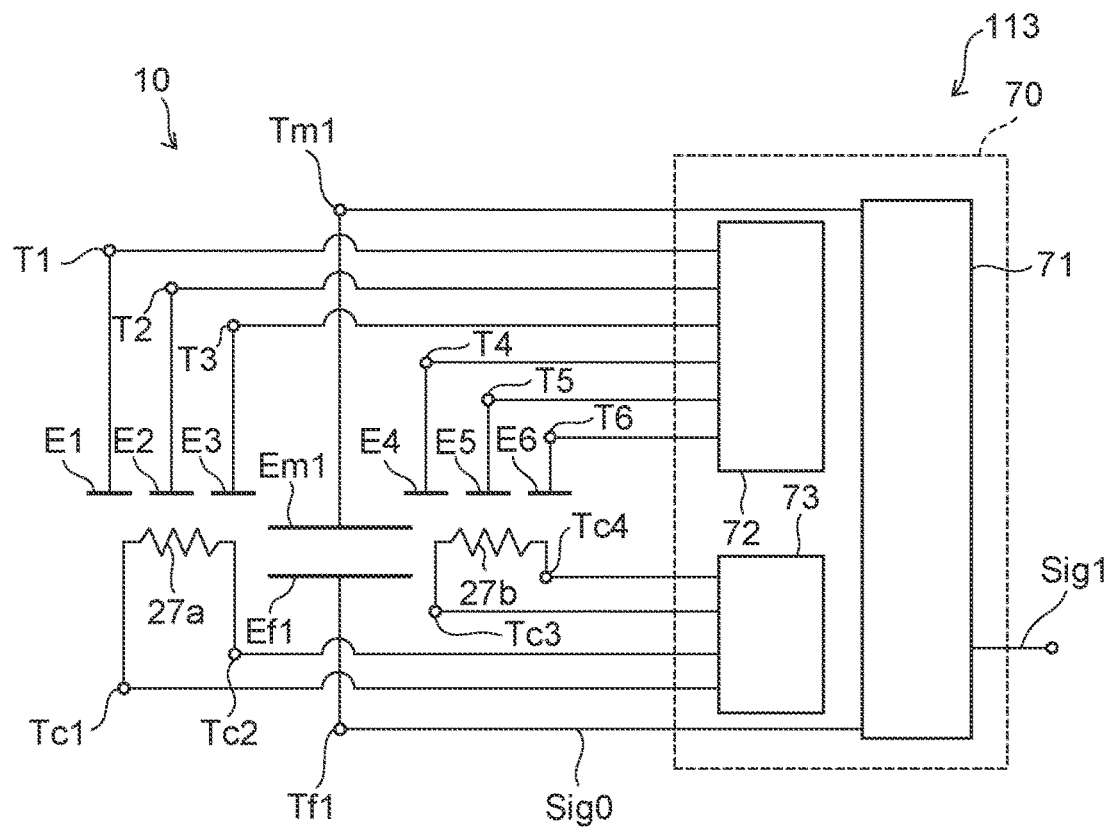

FIGS. 5A and 5B are schematic views illustrating a sensor according to a second embodiment.

FIG. 5A is a schematic cross-sectional view of the sensor 113 according to the embodiment. FIG. 5B is a schematic circuit diagram of the sensor 113.

As shown in FIGS. 5A and 5B, the sensor part 10 and the first circuit 70 are provided in the sensor 113 as well. The configuration described in reference to the sensor 110 are applicable to the sensor part 10 and the first circuit 70, The first support region 25a includes a first conductive layer 27a. As shown in FIG. 5A, the position in the first direction of the second electrode E2 is between the position in the first direction of the first electrode E1 and the position in the first direction of the first conductive layer 27a.

The sensor part 10 includes a first conductive terminal Tel and a second conductive terminal Tc2, The first conductive terminal Tc1 is connected with a portion of the first conductive layer 27a. The second conductive terminal Tc2 is connected with another portion of the first conductive layer 27a. At least a portion of the wiring that electrically connects the conductive terminals and the conductive layers may include conductive members provided in the supporter 23.

As shown in FIG. 5B, the first circuit 70 includes, for example, a conductive layer circuit 73. The conductive layer circuit 73 is electrically connected to the first conductive layer 27a via the first conductive terminal Tel. The conductive layer circuit 73 is electrically connected to the first conductive layer 27a via the second conductive terminal Tc2, A current is supplied between the first conductive terminal Tel and the second conductive terminal Tc2 from the first circuit 70 (the conductive layer circuit 73), The first circuit 70 is configured to perform a second operation of supplying a current to the first conductive layer 27a via the first conductive terminal Tel and the second conductive terminal Tc2.

The first conductive layer 27a is, for example, a heater. The temperature of the first conductive layer 27a increases when the current is supplied from the first circuit 70 to the first conductive layer 27a. By increasing the temperature of the first film 11 (in the example, the first electrode E1 and the third electrode E3) by the first conductive layer 27a, the first substance that is adhered or adsorbed to the first film 11 can be removed, and the detection speed of the first element can be increased.

In the example, the second support region 25b includes a second conductive layer 27b. As shown in FIG. 5A, the position in the first direction of the fifth electrode E5 is between the position in the first direction of the fourth electrode E4 and the position in the first direction of the second conductive layer 27b.

The sensor part 10 includes a third conductive terminal Tc3 and a fourth conductive terminal Tc4. The third conductive terminal Tc3 is connected with a portion of the second conductive layer 27b. The fourth conductive terminal Tc4 is connected with another portion of the second conductive layer 27b.

As shown in FIG. 53, the conductive layer circuit 73 is electrically connected to the second conductive layer 27b via the third conductive terminal Tc3. The conductive layer circuit 73 is electrically connected to the second conductive layer 27b via the fourth conductive terminal Tc4, A current is supplied between the third conductive terminal Tc3 and the fourth conductive terminal Tc4 from the first circuit 70 (the conductive layer circuit 73). The second operation of the first circuit 70 may include supplying a current to the second conductive layer 27h via the third conductive terminal Tc3 and the fourth conductive terminal Tc4. When the current is supplied from the first circuit 70 to the second conductive layer 27b (e.g, the heater), the first substance that is adhered or adsorbed to the first film 11 (in the example, the fourth electrode E4 and the sixth electrode E6) can be removed, and the detection speed of the first element, etc., can be improved.

Figure 6A:
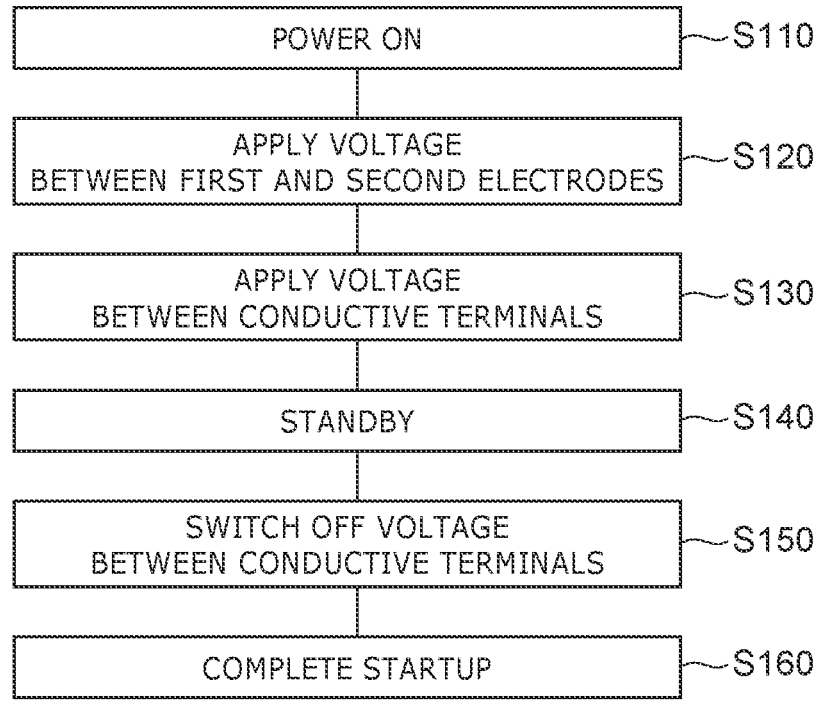
FIGS. 6A and 6B are flowcharts illustrating operations of the sensor according to the second embodiment.
Figure 6B:
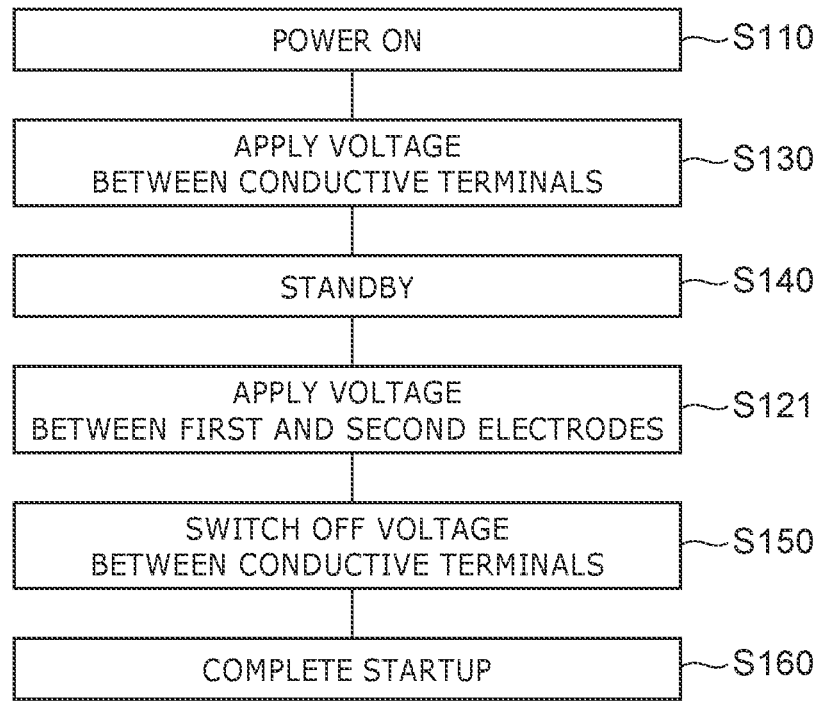

FIGS. 6A and 63 are flowcharts illustrating operations of the sensor according to the second embodiment.

FIGS. 6A and 63 show startup operation sequences of the sensor 113.

As shown in FIG. 6A, the sensor 113 is powered on (step S110). The first circuit 70 starts to perform the first operation of applying a voltage between the first electrode E1 and the second electrode E2 (step S120). Thereby, for example, an electric field is generated around the first electrode E1. For example, the adhesion of the first substance to the first electrode E1 can be suppressed.

The first circuit 70 applies a voltage between the first conductive terminal Tc1 and the second conductive terminal Tc2 (step S130). In other words, the first circuit 70 starts to perform the second operation of supplying a current to the first conductive layer 27a. The first circuit 70 waits (step S140). The temperature of the first conductive layer 27a is increased thereby. For example, the temperature of the first electrode E1 is Increased, and the first substance that is adhered or adsorbed to the first film 11 can be removed. The first circuit 70 switches off the voltage between the first conductive terminal Tel and the second conductive terminal Tc2 (step S150). In other words, the first circuit 70 ends the second operation. The startup of the sensor 113 is completed (step S160). After the startup is completed, the detection operation of the first element is performed. In the detection operation, the first operation of applying the voltage between the first electrode E1 and the second electrode E2 (step S120) that is performed in the startup operation is continued. Therefore, the adhesion or the adsorption of the first substance at the first film 11 is suppressed, and the detection performance of the first element is improved.

Thus, the first circuit 70 is configured to perform the second operation of supplying the current to the first conductive layer 27a after starting the first operation. For example, the first substance around the first electrode E1 can be controlled thereby, and the adhesion or the adsorption of the first substance can be suppressed. The first operation may be continued from step S120 to step S160. The second operation may be performed while performing the first operation. For example, the first circuit 70 may continue the first operation when detecting the concentration of the first element. For example, the detection sensitivity of the first element can be increased.

The voltage that is applied in the first operation includes, for example, a direct current component. The voltage that is applied in the first operation may include an alternating current component. The frequency of the alternating current component is, for example, not less than 100 kHz and not more than 1 MHz, not less than 20 MHz and not more than 50 MHz, or not less than 1 GHz and not more than 100 GHz. For example, the adhesion of the first substance to the first electrode E1 is easily suppressed thereby.

As shown in FIG. 68, step S121 may be performed instead of step S120. The first circuit 70 starts performing the first operation of applying the voltage between the first electrode E1 and the second electrode E2 (step S121) between step S140 and step S150, Thus, the first circuit 70 may start performing the first operation while performing the second operation. For example, the first substance around the first electrode E1 can be controlled thereby, and the adhesion or the adsorption of the first substance can be suppressed. For example, the detection sensitivity of the first element can be increased. The first operation may be continued from step S121 until step S160 ends. The first operation may be performed while performing the second operation. The detection operation of the first element is performed after the startup is completed. The first operation of applying the voltage between the first electrode E1 and the second electrode E2 (step S120) that is performed in the startup operation is continued in the detection operation. Therefore, the adhesion or the adsorption of the first substance at the first film 11 is suppressed, and the detection performance of the first element is improved.

Figure 7A:
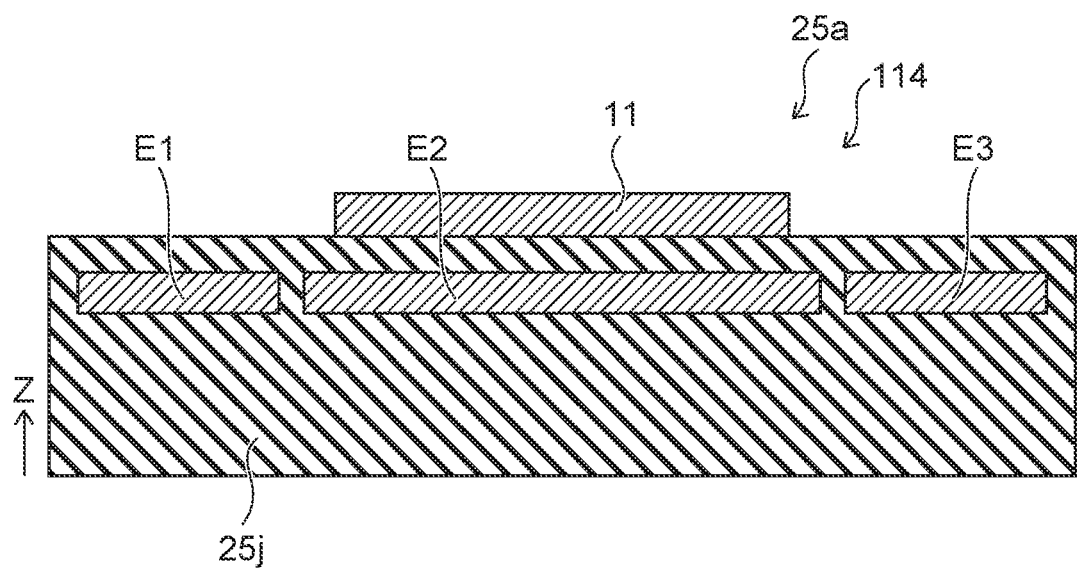
FIGS. 7A and 7B are schematic views illustrating a portion of another sensor according to the embodiment.
Figure 7B:
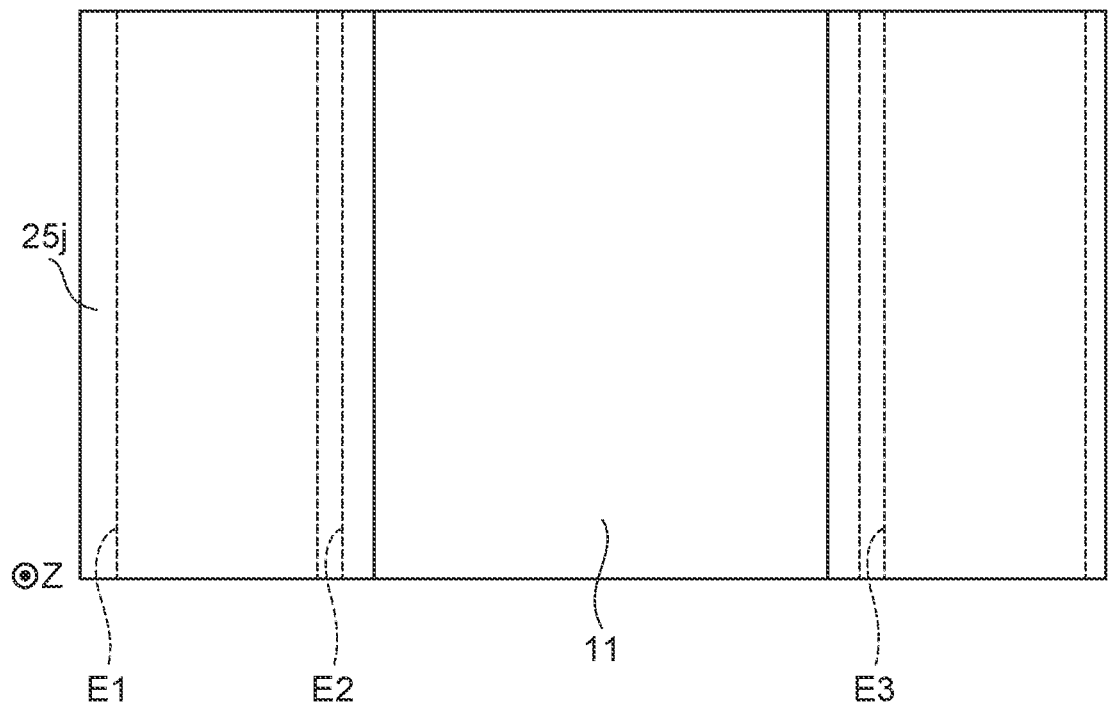

FIGS. 7A and 7B are schematic views illustrating a portion of another sensor according to the embodiment.

FIG. 7A is a schematic cross-sectional view of the first support region 25a of the sensor 114; and FIG. 7B is a schematic plan view of the first support region 25a of the sensor 114.

In the example, the first film 11 is provided separately from the first and third electrodes E1 and E3. The first electrode E1, the second electrode E2, and the third electrode E3 are arranged in a direction (e.g., the Y-axis direction) perpendicular to the Z-axis direction. The second electrode E2 is located between the first electrode E1 and the third electrode E3, A portion of the insulating portion 25j is located between the first electrode E1 and the second electrode E2 and between the second electrode E2 and the third electrode E3, The second electrode E2 is electrically insulated from the first and third electrodes E1 and E3.

At least a portion of the first film 11 overlaps the second electrode E2 in the Z-axis direction, A portion of the insulating portion 25j is located between the first film 11 and the first to third electrodes E1 to E3. The first film 11 and the first to third electrodes E1 to E3 are electrically insulated.

For example, the potential of the first electrode E1 and the potential of the third electrode E3 are set to be the same. An electric field can be generated between the first electrode E1 and the second electrode E2 and between the third electrode E3 and the second electrode E2 by the first operation of the first circuit 70. For example, the first substance around the first film 11 can be controlled by the generated electric field. The detection performance of the sensor can be improved thereby.

Otherwise, a description similar to the description of one of the sensors 110 to 113 described above is applicable to the sensor 114. The second support region 25b may be similar to the first support region 25a shown in FIGS. 7A and 7B.

Third Embodiment

Figure 8:
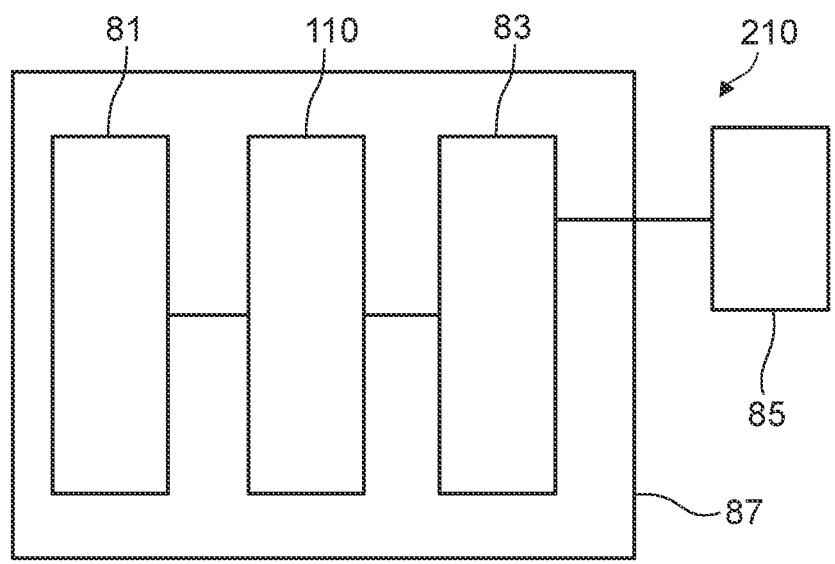
FIG. 8 is a block diagram illustrating a sensor according to a third embodiment.

FIG. 8 is a block diagram illustrating a sensor according to a third embodiment.

As shown in FIG. 8, the sensor module 210 according to the embodiment includes the sensor according to the embodiment (in the example, the sensor 110), a battery 81, a wireless communication circuit 83, an antenna 85, and a housing 87.

For example, the sensor 110, the battery 81, and the wireless communication circuit 83 are located inside the housing 87. At least a portion of the antenna 85 is located outside the housing 87. For example, the housing 87 is mounted to a ground surface, a floor, a wall, etc.

The battery 81 is connected to the sensor 110. The battery 81 is configured to supply electrical power to the sensor 110. The wireless communication circuit 83 is connected to the sensor 110. The wireless communication circuit 83 is configured to transmit a signal corresponding to a value detected by the sensor 110. The antenna 85 is connected with the wireless communication circuit 83. The signal is transmitted via the antenna 85.

Embodiments may include the following configurations (e.g., technological proposals), Configuration 1
A sensor, comprising:
a sensor part including
a base body,
a fixed electrode fixed to the base body,
a supporter fixed to the base body, and
a movable part supported by the supporter; and
a first circuit,
the movable part including
a movable region including a movable electrode facing the fixed electrode, and
a first support region provided between the movable region and the supporter,
the first support region including
a first electrode, and
a second electrode insulated from the first electrode,
the first circuit being configured to perform a first operation of applying a voltage between the first electrode and the second electrode.

Configuration 2
The sensor according to Configuration 1, wherein
a direction from the fixed electrode toward the movable electrode is along a first direction, and
at least a portion of the second electrode does not overlap the first electrode in the first direction, Configuration 3
The sensor according to Configuration 1, wherein
a direction from the fixed electrode toward the movable electrode is along a first direction, and
the second electrode does not overlap the first electrode in the first direction.

Configuration 4
The sensor according to Configuration 1, wherein
a direction from the fixed electrode toward the movable electrode is along a first direction, and
the first electrode overlaps the second electrode in the first direction, Configuration 5
The sensor according to Configuration 1, wherein
the first support region includes a first conductive layer,
the sensor part includes:
a first conductive terminal connected with a portion of the first conductive layer; and
a second conductive terminal connected with an other portion of the first conductive layer, and
a current is supplied between the first conductive terminal and the second conductive terminal.

Configuration 6
The sensor according to Configuration 5, wherein
a direction from the fixed electrode toward the movable electrode is along a first direction, and
a position in the first direction of the second electrode is between a position in the first direction of the first electrode and a position in the first direction of the first conductive layer.

Configuration 7
The sensor according to Configuration 5 or 6, wherein
a sensor signal is output from the sensor part and changes according to a concentration of a first element included in a gas around the sensor part, Configuration 8
The sensor according to any one of Configurations 5 to 7, wherein
the first circuit also is configured to perform a second operation of supplying a current to the first conductive layer, and
the first circuit performs the second operation after starting the first operation.

Configuration 9
The sensor according to any one of Configurations 5 to 7, wherein
the first circuit also is configured to perform a second operation of supplying a current to the first conductive layer, and
the first circuit starts performing the first operation while performing the second operation.

Configuration 10
The sensor according to any one of Configurations 1 to 6, wherein
a gap is provided between the fixed electrode and the movable electrode, and
a distance of the gap changes according to a concentration of a first element included in a gas around the sensor part, Configuration 11
The sensor according to any one of Configurations 1 to 6, wherein
an electrostatic capacitance between the movable electrode and the fixed electrode changes according to a concentration of a first element included in a gas around the sensor part.

Configuration 12
The sensor according to any one of Configurations 1 to 6, wherein
a shape of the first electrode changes according to a concentration of a first element included in a gas around the sensor part.

Configuration 13
The sensor according to any one of Configurations 1 to 6, wherein
the first support region includes a first film insulated from the first and second electrodes, and
a shape of the first film changes according to a concentration of a first element included in a gas around the sensor part.

Configuration 14
The sensor according to any one of Configurations 1 to 13, wherein
the first support region includes a third electrode insulated from the second electrode, and
the first operation includes applying a voltage between the second electrode and the third electrode.

Configuration 15
The sensor according to Configuration 14, wherein
a second direction from the first support region toward the movable region crosses a first direction from the fixed electrode toward the movable electrode,
a third direction from the first electrode toward the third electrode crosses a plane including the first and second directions, and
a position in the third direction of at least a portion of the second electrode is between a position in the third direction of the first electrode and a position in the third direction of the third electrode.

Configuration 16
The sensor according to any one of Configurations 1 to 15, wherein
the first electrode surrounds the second electrode when viewed along a first direction from the fixed electrode toward the movable electrode.

Configuration 17
The sensor according to any one of Configurations 1 to 16, wherein
the movable part includes a second support region,
the movable region is between the first support region and the second support region,
the second support region includes:
a fourth electrode; and
a fifth electrode insulated from the fourth electrode, and
the first operation includes applying a voltage between the fourth electrode and the fifth electrode.

Configuration 18
The sensor according to Configuration 17, wherein
the second support region includes a sixth electrode insulated from the fifth electrode, and
the first operation includes applying a voltage between the fifth electrode and the sixth electrode.

Configuration 19
The sensor according to Configuration 18, wherein
a second direction from the first support region toward the movable region crosses a first direction from the fixed electrode toward the movable electrode,
a fourth direction from the fourth electrode toward the sixth electrode crosses a plane including the first and second directions, and
a position in the fourth direction of at least a portion of the fifth electrode is between a position in the fourth direction of the fourth electrode and a position in the fourth direction of the sixth electrode.

Configuration 20
The sensor according to any one of Configurations 1 to 19, wherein
the first electrode includes at least one selected from the group consisting of Pd, Pt, and Au.

Configuration 21
The sensor according to any one of Configurations 1 to 20, wherein
the voltage between the first electrode and the second electrode includes an alternating current component.

Configuration 22
The sensor according to Configuration 21, wherein
a frequency of the alternating current component is not less than 100 kHz and not more than 1 MHz, not less than 20 MHz and not more than 50 MHz, or not less than 1 GHz and not more than 100 GHz.

According to embodiments, a sensor can be provided in which the detection performance can be improved.

In the specification, "electrically connected" also includes the case of being connected via other conductive members in addition to the case of being connected with direct contact.

In the specification of the application, "perpendicular" and "parallel" refer to not only strictly perpendicular and strictly parallel but also include, for example, the fluctuation due to manufacturing processes, etc. It is sufficient to be substantially perpendicular and substantially parallel.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in sensors such as sensor parts, first circuits, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all sensors practicable by an appropriate design modification by one skilled in the art based on the sensors described above as embodiments of the invention also are within the scope of the invention to the extent that the spirit of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention,

What is claimed is:

1. A sensor, comprising:
a sensor part including
a base body,
a fixed electrode fixed to the base body,
a supporter fixed to the base body, and
a movable part supported by the supporter; and
a first circuit,
the movable part including
a movable region including a movable electrode facing the fixed electrode, and
a first support region provided between the movable region and the supporter,
the first support region including
a first electrode, and
a second electrode insulated from the first electrode,
the first circuit being configured to perform a first operation of applying a voltage between the first electrode and the second electrode.

2. The sensor according to claim 1, wherein
a direction from the fixed electrode toward the movable electrode is along a first direction, and
at least a portion of the second electrode does not overlap the first electrode in the first direction.

3. The sensor according to claim 1, wherein
a direction from the fixed electrode toward the movable electrode is along a first direction, and
the second electrode does not overlap the first electrode in the first direction.

4. The sensor according to claim 1, wherein
a direction from the fixed electrode toward the movable electrode is along a first direction, and
the first electrode overlaps the second electrode in the first direction.

5. The sensor according to claim 1, wherein
the first support region includes a first conductive layer, the sensor part includes:
a first conductive terminal connected with a portion of the first conductive layer; and
a second conductive terminal connected with an other portion of the first conductive layer, and
a current is supplied between the first conductive terminal and the second conductive terminal.

6. The sensor according to claim 5, wherein
a direction from the fixed electrode toward the movable electrode is along a first direction, and
a position in the first direction of the second electrode is between a position in the first direction of the first electrode and a position in the first direction of the first conductive layer.

7. The sensor according to claim 5, wherein
a sensor signal is output from the sensor part and changes according to a concentration of a first element included in a gas around the sensor part.

8. The sensor according to claim 5, wherein
the first circuit also is configured to perform a second operation of supplying a current to the first conductive layer, and
the first circuit performs the second operation after starting the first operation.

9. The sensor according to claim 5, wherein
the first circuit also is configured to perform a second operation of supplying a current to the first conductive layer, and
the first circuit starts performing the first operation while performing the second operation.

10. The sensor according to claim 1, wherein
a gap is provided between the fixed electrode and the movable electrode, and
a distance of the gap changes according to a concentration of a first element included in a gas around the sensor part.

11. The sensor according to claim 1, wherein
an electrostatic capacitance between the movable electrode and the fixed electrode changes according to a concentration of a first element included in a gas around the sensor part.

12. The sensor according to claim 1, wherein
a shape of the first electrode changes according to a concentration of a first element included in a gas around the sensor part.

13. The sensor according to claim 1, wherein
the first support region includes a first film insulated from the first and second electrodes, and
a shape of the first film changes according to a concentration of a first element included in a gas around the sensor part.

14. The sensor according to claim 1, wherein
the first support region includes a third electrode insulated from the second electrode, and
the first operation includes applying a voltage between the second electrode and the third electrode.

15. The sensor according to claim 14, wherein
a second direction from the first support region toward the movable region crosses a first direction from the fixed electrode toward the movable electrode,
a third direction from the first electrode toward the third electrode crosses a plane including the first and second directions, and
a position in the third direction of at least a portion of the second electrode is between a position in the third direction of the first electrode and a position in the third direction of the third electrode.

16. The sensor according to claim 1, wherein
the first electrode surrounds the second electrode when viewed along a first direction from the fixed electrode toward the movable electrode.

17. The sensor according to claim 1, wherein
the movable part includes a second support region,
the movable region is between the first support region and the second support region,
the second support region includes:
 a fourth electrode; and
 a fifth electrode insulated from the fourth electrode, and
the first operation includes applying a voltage between the fourth electrode and the fifth electrode.

18. The sensor according to claim 17, wherein
the second support region includes a sixth electrode insulated from the fifth electrode, and
the first operation includes applying a voltage between the fifth electrode and the sixth electrode.

19. The sensor according to claim 18, wherein
a second direction from the first support region toward the movable region crosses a first direction from the fixed electrode toward the movable electrode,
a fourth direction from the fourth electrode toward the sixth electrode crosses a plane including the first and second directions, and
a position in the fourth direction of at least a portion of the fifth electrode is between a position in the fourth direction of the fourth electrode and a position in the fourth direction of the sixth electrode.

20. The sensor according to claim 1, wherein
the first electrode includes at least one selected from the group consisting of Pd, Pt, and Au.

* * * * *